United States Patent [19]
Blunck

[11] 3,950,644
[45] Apr. 13, 1976

[54] NON-DISPENSIVE INFRARED GAS ANALYZER

[75] Inventor: Otto Blunck, Hamburg, Germany

[73] Assignee: H. Maihak AG, Hamburg, Germany

[22] Filed: June 28, 1974

[21] Appl. No.: 484,336

[30] Foreign Application Priority Data
July 2, 1973 Germany............................ 2333664

[52] U.S. Cl.................................. 250/343; 356/51
[51] Int. Cl.² ......................................... G01N 21/26
[58] Field of Search .......... 250/343, 344, 345, 346, 250/373; 356/51

[56] References Cited
UNITED STATES PATENTS
3,105,147  9/1963  Weilbach............................ 250/344
3,162,761  12/1964  Luft.................................... 250/344

*Primary Examiner*—Craig E. Church
*Attorney, Agent, or Firm*—Michael J. Striker

[57] ABSTRACT

A non-dispersive infrared analyzer, particularly for determining the concentration of a gas in a gas mixture, including a source of infrared radiation, means for modulating the radiation beam, a test chamber in the path of the modulated beams and containing the gas to be analyzed; an absorption chamber in the path of the beams exiting the test chamber, including a forward and a rear portion through which the beams sequentially traverse; and a vaned adjustment structure located in the rear portion of the absorption chamber for adjusting the path length of the beams in the rear portion of the absorption chamber.

16 Claims, 8 Drawing Figures

NON-DISPENSIVE INFRARED GAS ANALYZER

BACKGROUND OF THE INVENTION

The present invention relates generally to a non-dispersive infrared analyzing apparatus for measuring the concentration of a gas in a gas mixture, and more particularly to one utilizing a modulated infrared radiation beam.

The use of a modulated infrared beam to analyse a gas mixture by means of a double-celled test chamber is already well known in the prior art. Such arrangements make use of a double-layered absorption or detection chamber, in which the modulated beam traverses sequentially first a forward portion or layer, and then a rear portion or layer. The path length of the radiation beam in the forward portion is shorter than the path length in the rear portion.

In such gas analyzers, the predominant energy absorbed is associated with the most probable wavelength ranges, for example in the center of the absorption line spectrum. In the rear portion or layer, the less probable side spectrum line regions would be absorbed. This is possible since the forward layer has already absorbed the radiation corresponding to the easily absorbable wavelength regions. The difference in the absorption of beam energy of the radiation corresponding to the two cells of the test chamber is a measure of the concentration of the analyzed gas in the gas mixture.

The null point of the measurement, corresponding to a zero concentration of the analyzed gas in the gas mixture, must result in a zero output signal. This therefore implies that the measurement of the null point of the pressure impulse based on the absorption of the modulated beams in both of the provided layers, must be equalized both in terms of amplitude and phase, and the membrane condensor adjusted to a dynamical operating balance.

As a result of the absorption of the modulated beam in the absorption chamber, a pressure impulse is created depending on the total volume and the absorbed power level. The time lag of the pressure impulses and therefore the phase lag will essentially be determined by the heating and cooling effect depending on the volume as well as the heat conductivity of the measuring chamber for the particular gas or gases under consideration. The equalizing of the impulse amplitudes is achieved by selecting the length of the absorption chamber as well as the partial pressure, in addition to providing a non-cylindrical geometry for the rear portion. But because of the different geometry of the chamber, different capillary diameters, as well as the differences in the characteristics of the gas in both layers, there are different time constants for heating and cooling; the equalization of the pressure impulses in such prior known devices is therefore not perfect. The inequality originates from a phase difference between the signal from the forward and the rear layer of the absorption cell, even producing a resulting difference signal from full amplitude equalization which is larger than the difference of respective end range values for the signal being measured.

Even with the most close fitting parts and uniform production and packing techniques for the measurement chamber, absolute symmetry is not achieved, since the symmetry is effected by the beam geometry and the wavelength-dependent beam intensity, for example, the emitter temperature.

It is desirable to obtain an exact equalization both in terms of the amplitudes and the phases of the pressure impulses between both forward and rear portions of the absorption chamber. It is particularly advantageous to achieve this equalization for the amplitude and phase in a simple and practical manner. There have been attempts to provide full equalization through interfering with the beam geometry by means of an adjustable shield before the absorption chamber. However, in such a situation the absorbed energy in both of the layers would vary and at the same time there would be an undesirable variation in the range of the sample or measured signal.

Furthermore, the placing of a shield between the absorption layers or cells does not result in any satisfactory solution to the problem affecting the amplitudes of pressure impulses, though the different phase differences corresponding to different cooling and heating times would scarcely vary. Another method is to attempt an equalization by means of a pneumatic shunt or a storage buffer. Such an arrangement is, however, expensive and inconvenient and a loss of sensitivity is associated with the increased volume.

The same process is also applicable to the method of equalizing the pressure impulses of each absorption layer by means of a passive equalization volume, which is matched with the volume of the other absorption layer by means of a connecting condensor membrane. In this case there is a diminution of the signal by a factor $V_1/(V_1 + V$ passive volumer).

It has also been proposed to connect both absorption layers by means of an axially moveable window operable from outside the measuring chamber, or utilizing between both absorption layers a compensation layer with an adjustable gas pressure. With the help of such an arrangement, it is possible to equalize the amplitude of the signals while the geometry of the layers, and therefore the heating and cooling times, remain unchanged, and the phase equalization is not achieved. Moreover, it follows from the first solution through the variation of the volume of both chambers a variation in the measurement range results.

Another method is to compensate for the different amplitude and phases by means of a difference signal which utilizes an adjustable amplitude and phase factor to thereby adjust the parameters to the null point measurement. This is, however, a relatively complicated method.

It is also known to provide a metal cone in the interior of the rear absorption cell or layer, and adjust its axial position. With this method only the rear absorption layer will be influenced, so that no signal diminution or sensitivity variation would arise. However, the variation of the position of the cone will influence the amplitude or magnitude of the pressure impulses, though the influence on the phase will likewise be small.

SUMMARY OF THE INVENTION

It is an object of the invention to provide a non-dispersive infrared analyzer, particularly for determining the concentration of a gas in a gas mixture, which overcomes the disadvantages of the prior art.

It is another object of the invention to provide a non-dispersive infrared analyzer in which the rear layer of the absorption measurement chamber is provided with a member with vane-like portions.

Another object of the invention is to provide a nondispersive infrared analyzer, comprising a source of infrared radiation producing a radiation beam; means for modulating said beam; a test chamber in the path of said modulated beam containing the gas to be analyzed; an absorption chamber in the path of the beam exiting said test chamber, comprising a forward and a rear portion or layer to which the beams traverse sequentially; and adjustment means located in said rear portion for adjusting the path length of said beam in said rear portion.

The adjustment means comprises a member with one or more vane-like portions. Preferably the member is rotatable on its axis and slidable along its axis.

In another embodiment of the invention, the vane-like portions of the member are pivotable to different positions, whereby the pivoting action can be adjusted from outside of the measuring chamber by a user. Preferably the body with the vane-like portions is constructed of a heat conducting material, and may also be constructed with an optically reflecting outer surface.

The invention is therefore directed at providing a simple device for adjusting the measurement chamber pressures to exact equalization, without varying the sensitivity of the measuring chamber and permitting the amplitude and phase to be varied with respect to one another in a practical manner. The arrangement provides that the absorbing volume in the rear layer would be varied on the one hand, while on the other hand the heating and cooling process in the rear layer could also be periodically influenced.

The present apparatus permits an exact null point equalization for both amplitide and phase to be achieved. Therefore the analyzer is usable over a smaller or narrower measuring range than other analyzers, while also maintaining good stability over long periods of time. Signal diminution and loss of sensitivity are prevented.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
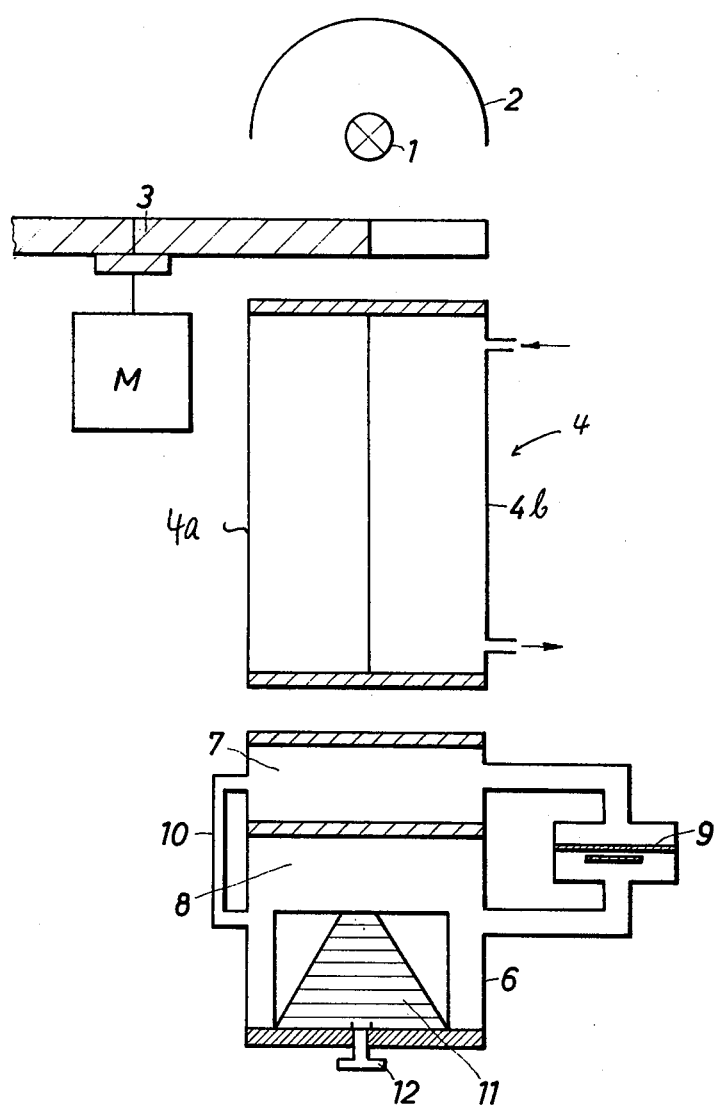
FIG. 1 illustrates a highly schematic view of an infrared gas analyzer apparatus as taught by the present invention.

FIG. 1 illustrates an infrared gas analyzing apparatus, including an infrared radiation source 1, a reflector 2 placed behind the radiation source, a rotating diaphragm or screen 3, operatively attached to a motor M for modulation of the emitted infrared radiation beam. The modulated beam will then pass through the reference chamber 4a and the sample or measurement chamber 4b of a cuvette 4 in predetermined phase relationship. The beams then fall on the absorption measurement chamber 6, comprising a forward absorption cell 7 and a rear absorption cell 8. The two absorption cells are connected by means of a membrane condensor 9. Any existing statistically varying pressure difference between the absorption chambers 7 and 8 would be equalized by means of a connecting capillary tube 10. In the interior of the rear absorption cell 8 is an arrangement of adjustable vane-like portions or sections, which are adjustable both in terms of depth into the chamber as well as angular position by means of a jack screw 12.

Figure 2A:
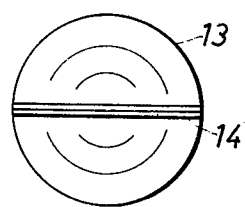
FIGS. 2a, 2b and 2c illustrate the particular forms taken by the vane-like members utilized in the present invention.
Figure 2B:
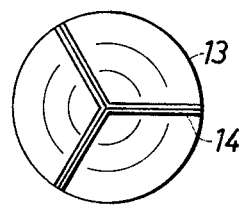
Figure 2C:
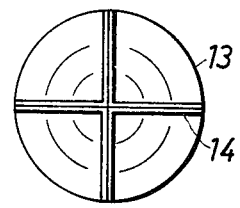

FIGS. 2a, 2b and 2c are representations of the position of the vane-like members as seen from the top. On the side portions of the cone or truncated cone segment 13 are one, two (FIG. 2a), three (FIG. 2b), four (FIG. 2c), or more vanes 14 attached. The structure 11 can have other forms in addition to that of a cone; one can, for example, utilize a plurality of vanes without having a central support structure.

Figure 3:
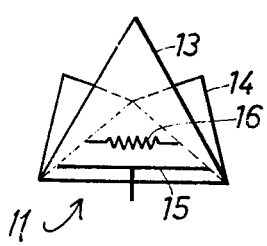
FIG. 3 is a side view of the folding mechanism of the vane-like members.

FIG. 3 illustrates a structure 11 with pivoting vanes 14, whose position with respect to the cone 13 can be pivoted or varied by means of the pivot control device 15 in combination with a spring 16 connecting two of the vanes.

Figure 4A:
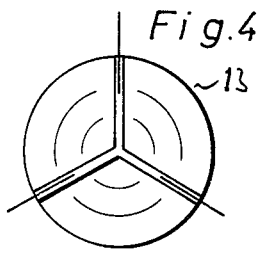
FIGS. 4a and 4b are another representation of the wing-like members with three (4a) or four (4b) vanes.
Figure 4B:
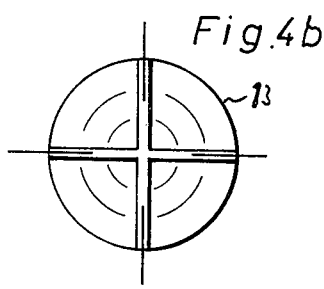

FIGS. 4a and 4b are additional embodiments of the vaned structure utilizing three (FIG. 4a) or four (FIG. 4b) vanes.

The operation of the apparatus according to the principles of the present invention is as follows:

The adjustment of the vaned structure 11 by means of the screw 12 permits the operator to vary the volume in the rear absorption cell 8 in which the vaned structure 11 is situated. Such a change affects the amplitude of the pressure signals obtained from the rear cell 8. The amplitude of the pressure signals from the forward cell 7 is not affected. In this manner, one can adjust the amplitude of the pressure signals from the rear cell 8 to the level of the pressure signals from the forward cells 7 by means of adjusting the level of the vaned structure 11. In the arrangement as shown in the drawings, in which two beams pass through a partitioned cuvette 4, one can adjust the phase between the two beams through rotation of the vaned structure 11. By means of rotation of the conical body 11 will the vanes be situated in different positions with respect to both centers of the two beams corresponding with the two portions of the cuvette 4. The screw 12 serves as a fine adjustment device for varying the position of the vaned structure 11 in the rear portion or cell of the absorption chamber 6. Both the angular position of the vanes, as well as the depth of penetration of the vane structure 11 into the rear portion or cell 8 can be adjusted. In this manner, the length of the travel path of the incoming radiation beams passing through the rear chamber 8 may be carefully adjusted and varied. In this manner it is possible to adjust the phase of the pressure impulses in the rear chamber 8 with those in the forward chamber 7.

Figure 5:
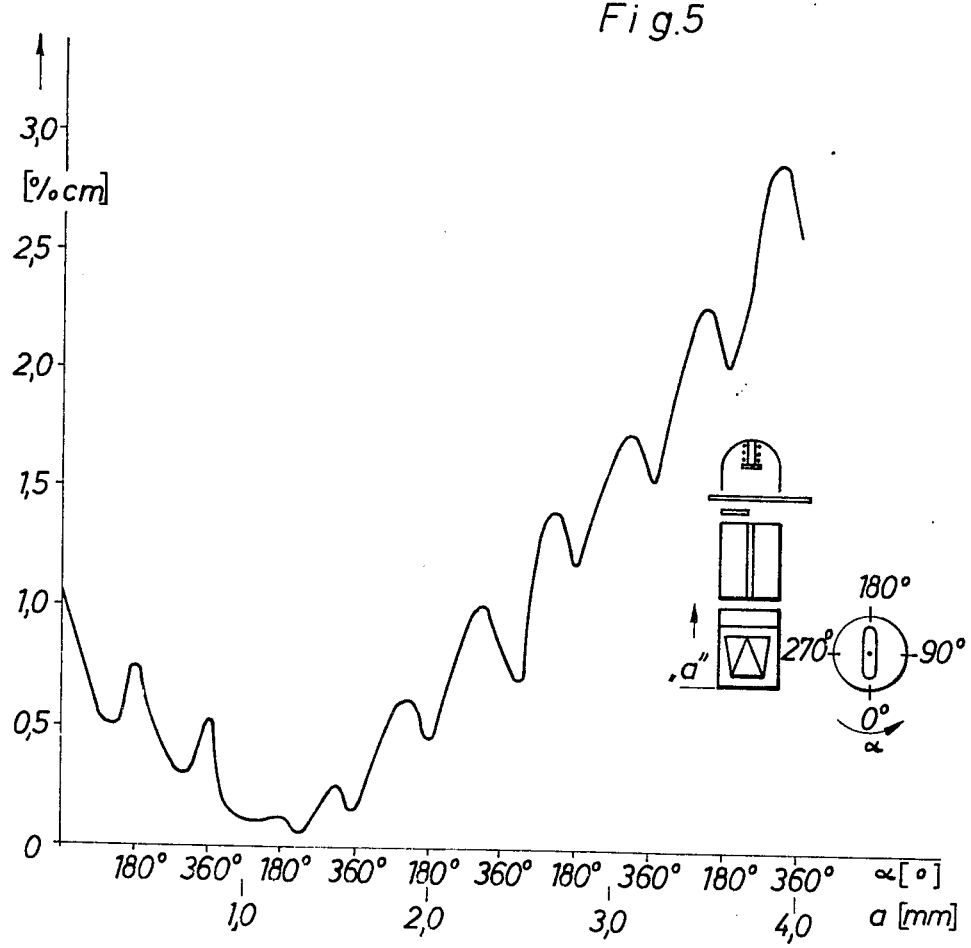
FIG. 5 is a graph of the differential signal of methane concentration plotted against the various linear and angular positions of the vane members utilized in the present apparatus.

FIG. 5 illustrates the outcome of the adjustment of the vaned structure over a wide variety of angles and penetration depths. A reduced and highly simplified sketch of the apparatus is shown, indicating the penetration depth $a$, as well as the angular position $\alpha$ of the vaned structure, with reference to the rear absorption cell 8. The graph in FIG. 5 is a plot of these two quantities $a$ and $\alpha$ corresponding to various adjustments of the vaned structure 11, with respect to the differential signal of a methane ($CH_4$) chamber. The graph is calibrated in terms of the amplitude of the difference signal as measured in percent times centimeter. The curve clearly indicates both a large-scale and a fine-scale structure. The large-scale structure is controlled by the penetration depth of the vaned structure 11, whereas the angular position of the structure 11 determines the superimposed fine-scale structure. By means of the angular adjustment provided by the jack screw 12, it is possible to obtain a fine regulation of the difference signal to an extremely small value, as low as 0.03 percent cm in the particular case illustrated.

The present invention can also be utilized with an arrangement providing only for a single beam, i.e. a single chamber cuvette. In such a case one may preferably utilize an adjustment structure with pivotable vanes, in order to adjust the thermal time constant of the radiation beam passing through the absorption cell. The utilization of pivoted vanes with the two beam apparatus, such as illustrated in FIG. 1, is another improvement in the sensitivity and operation of the apparatus.

It will be understood that each of the elements described above, or two or more together, may also find a useful application in other types of apparatus differing from the types described above.

While the invention has been illustrated and described as embodied in a non-dispersive infrared analyzer, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A non-dispersive infrared analyzer, particularly for determining the concentration of a gas in a gas mixture, comprising, in combination, a source of infrared radiation using a radiation beam; means for modulating said beam; a test chamber in the path of said modulated beam containing the gas to be analyzed; an absorption chamber in the path of the beam exiting said test chamber, comprising a forward and a rear portion which the beam suquentially traverses producing pressure changes in the forward and rear portions dependent upon the concentration of the gas being measured and upon the modulation of the beam; and in said rear portion a structure mounted to have an adjustable orientation and so configurated that changes of the orientation of said structure change the phase difference between the pressure changes in the forward and rear portions of the absorption chamber.

2. An analyzer as defined in claim 1, wherein said structure is rotatably mounted and so configurated that changes of the angular orientation of said structure change the phase difference between the pressure changes in the forward and rear portions of the absorption chamber.

3. An analyzer as defined in claim 2, wherein said structure is furthermore mounted for longitudinal adjusting movement along the axis of rotation thereof.

4. An analyzer as defined in claim 3, wherein said structure is mounted for interdependent longitudinal and rotational adjusting movement.

5. An analyzer as defined in claim 2, wherein said structure has at least one radial vane.

6. An analyzer as defined in claim 1, wherein said structure has at least one vane.

7. A non-dispersive infrared analyzer, particularly for determining the concentration of a gas in a gas mixture, comprising, in combination, a source of infrared radiation using a radiation beam; means for modulating said beam; a test chamber in the path of said modulated beam containing the gas to be analyzed; an absorption chamber in the path of the beam exiting said test chamber, comprising a forward and a rear portion which the beam sequentially traverses; and in said rear portion a vaned structure provided with at least one vane-like portion for establishing the geometry of the interior of said rear portion.

8. An analyzer as defined in claim 7, wherein said vaned structure is provided with a plurality of vane-like portions.

9. An analyzer as defined in claim 7, wherein said vaned structure is rotatably mounted for angular adjustment.

10. An analyzer as defined in claim 7, wherein said vaned structure is shiftably mounted for longitudinal adjustment.

11. An analyzer as defined in claim 7, wherein the material of said vaned structure is a thermal conductor.

12. An analyzer as defined in claim 7, wherein said vaned structure has a light reflecting surface.

13. An analyzer as defined in claim 7, wherein said at least one vane-like portion is pivotally mounted on said structure for pivotal adjustment.

14. An analyzer as defined in claim 13, wherein said at least one pivotally mounted vane-like portion is adjustable from outside said absorption chamber.

15. A non-dispersive infrared analyzer, particularly for determining the concentration of a gas in a gas mixture, comprising in combination a source of infrared radiation using a radiation beam; means for modulating said beam; a test chamber in the path of said modulated beam containing the gas to be analyzed; an absorption chamber in the path of the beam exiting said test chamber, comprising a forward and a rear portion which the beam sequentially traverses; and adjustment means located in said rear portion for adjusting the path length of said beam in said rear portion, wherein said adjustment means comprises a structure having at least one vane, wherein said structure has an axis substantially in the direction of the path of the radiation beam, said structure being rotatable and angularly adjustable about said axis.

16. A non-dispersive infrared analyzer, particularly for determining the concentration of a gas mixture, comprising in combination a source of infrared radiation using a radiation beam; means for modulating said beam; a test chamber in the path of said modulated beam containing the gas to be analyzed; an absorption chamber in the path of the beam exiting said test chamber, comprising a forward and a rear portion which the beam sequentially traverses; and adjustment means located in said rear portion for adjusting the path length of said beam in said rear portion, wherein said adjustment means comprises a structure having vanes, and wherein said vanes are pivotably attached to said structure.

* * * * *